United States Patent
MacLachlan et al.

(10) Patent No.: US 8,329,070 B2
(45) Date of Patent: Dec. 11, 2012

(54) LIPOSOMAL APPARATUS AND MANUFACTURING METHOD

(75) Inventors: Ian MacLachlan, Mission (CA); Lloyd Jeffs, Burnaby (CA); Lorne R. Palmer, Burnaby (CA); Cory Giesbrecht, Vancouver (CA); Noelle Giesbrecht, legal representative, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 0 days.

(21) Appl. No.: 12/965,555

(22) Filed: Dec. 10, 2010

(65) Prior Publication Data

US 2011/0216622 A1    Sep. 8, 2011

Related U.S. Application Data

(62) Division of application No. 10/611,274, filed on Jun. 30, 2003, now Pat. No. 7,901,708.

(60) Provisional application No. 60/392,887, filed on Jun. 28, 2002.

(51) Int. Cl.
*A61K 9/127* (2006.01)
*A61K 31/52* (2006.01)
*A61K 31/519* (2006.01)

(52) U.S. Cl. ....... 264/4.1; 264/4.3; 424/450; 514/263.1; 514/264.1

(58) Field of Classification Search .............. 264/4.1, 264/4.3; 424/450; 514/263.1, 264.1
See application file for complete search history.

(56) References Cited

U.S. PATENT DOCUMENTS

| | | | |
|---|---|---|---|
| 4,687,661 | A | 8/1987 | Kikuchi et al. |
| 5,478,860 | A | 12/1995 | Wheeler et al. |
| 5,552,157 | A | 9/1996 | Yagi et al. |
| 5,653,996 | A | 8/1997 | Hsu |
| 5,885,613 | A | 3/1999 | Holland et al. |
| 5,976,567 | A | 11/1999 | Wheeler et al. |
| 5,981,501 | A | 11/1999 | Wheeler et al. |
| 6,093,348 | A * | 7/2000 | Kowalski et al. .......... 252/363.5 |
| 6,835,395 | B1 | 12/2004 | Semple et al. |
| 6,843,942 | B2 | 1/2005 | Katinger et al. |
| 7,341,738 | B2 * | 3/2008 | Semple et al. ............... 424/450 |
| 7,641,915 | B2 | 1/2010 | Chen et al. |
| 2003/0077829 | A1 | 4/2003 | MacLachlan |
| 2003/0124033 | A1 | 7/2003 | Baker et al. |
| 2004/0032037 | A1 | 2/2004 | Katinger et al. |

(Continued)

FOREIGN PATENT DOCUMENTS

CA        2041075 A1    10/1991

(Continued)

OTHER PUBLICATIONS

Hirota et al. "Simple Mixing Device to Reproducibly Prepare Cationic Lipid-DNA Complexes (Lipoplexes)," Biotechniques Aug. 1999, 27, pp. 286-290.*

(Continued)

*Primary Examiner* — James H. Alstrum-Acevedo
(74) *Attorney, Agent, or Firm* — Kilpatrick Townsend & Stockton LLP

(57) ABSTRACT

The present invention provides apparatus and processes for producing liposomes. By providing a buffer solution in a first reservoir, and a lipid solution in a second reservoir, continuously diluting the lipid solution with the buffer solution in a mixing chamber produces a liposome. The lipid solution preferably comprises an organic solvent, such as a lower alkanol.

13 Claims, 15 Drawing Sheets

U.S. PATENT DOCUMENTS

| | | | |
|---|---|---|---|
| 2004/0037874 | A1 | 2/2004 | Hong et al. |
| 2006/0058249 | A1 | 3/2006 | Tong et al. |
| 2008/0200417 | A1 | 8/2008 | Semple et al. |
| 2009/0191259 | A1 | 7/2009 | Li et al. |

FOREIGN PATENT DOCUMENTS

| | | | |
|---|---|---|---|
| CA | 2427640 A1 | | 5/2003 |
| EP | 0 055 576 A1 | | 7/1982 |
| EP | 1 013 268 A | | 6/2000 |
| EP | 1203614 A1 | * | 11/2000 |
| IE | 911350 | | 4/1991 |
| WO | WO 89/07929 A1 | | 9/1989 |
| WO | WO 91/16039 A1 | | 10/1991 |
| WO | WO 96/40964 A2 | | 12/1996 |
| WO | WO 00/29103 A1 | | 5/2000 |
| WO | WO 01/05373 A1 | | 1/2001 |
| WO | WO 02/43699 A2 | | 6/2002 |
| WO | WO 2004/002453 | * | 1/2004 |

OTHER PUBLICATIONS

Zelphati et al. "Stable and monodisperse lipoplex formulations for gene delivery," Gene Therapy 1998, 5, pp. 1272-1282.*

Isele et al. "Large-Scale Production of Liposomes Containing Monomeric Zinc Phthalocyanine by Controlled Dilution of Organic Solvents," Journal of Pharmaceutical Sciences, Nov. 1994, 83(11), pp. 1608-1616.*

Batzri et al. "Single Bilayer Liposomes Prepred without Sonication," Biochimica et Biophysica acta 1973, vol. 298, pp. 1015-1019.

Georgopapadakou, N. H., ed., "Drug Transport in Antimicrobial and Anticancer Chemotherapy," CRC Press, Marcel Dekker, Inc. (1995).

MacLachlan; Liposomal Formulations for Nucleic Acid Delivery; Antisense Drug Technologies, Second Edition; 2007; pp. 237-270.

Maurer et al. "Spontaneous Entrapment of Polynucleotides upon Electrostatic Interaction with Ethanol-Destabilized Cationic Liposomes," Biological Journal, May 2001, vol. 80, pp. 2310-2326.

Paul et al. "Effective expression of small interfering RNA in human cells," Nature Biotechnology, May 2002, vol. 20, pp. 505-508.

Semple et al. "Efficient encapsulation of antisense oligonucleotides in lipid vesicles using ionizable aminolipids: formation of novel small multilamellar vesicle structures," Biochim. Biophys. Acta, 2001, vol. 1510, No. 1-2, pp. 152-166.

Szoka et al. "Comparative Properties and Methods of Preparation of Lipid Vesicles (liposomes)," Ann. Rev. Biophys. Bioeng. 1980, vol. 9, pp. 467-508.

Wagner et al. "The Crossflow Injection Technique: an Improvement of the Ethanol Injection Method," Journal of Liposome Research, Sep. 2002, vol. 12, No. 3, pp. 259-270.

Wheeler et al. "Stabilized plasmid-lipid particles: construction and characterization," Gene Ther., 1999, vol. 6, No. 2, pp. 271-281.

First Action Interview Pilot Program Pre-Interview Communication dated Aug. 27, 2010 issued in U.S. Appl. No. 11/495,150, filed Jul. 27, 2006. (4 pages).

* cited by examiner rF before Triton = 0.4 & rF after Triton = 4.0

Therefore, calcein is: (1) encapsulated within the vesicle
(2) self quenching at the current concentration

Conditions and Properties for SPLP and Liposome Formation

Note: all samples prepared at 37°C

| Sample Description | Q Flow rate (L/min) | D Orifice ID (cm) | Vesicle Size (nm) | Size Std Dev (nm) | χ2 | Linear Velocity (m/s) | Shear Rate (s$^{-1}$) | Reynolds number | N/dN/d |
|---|---|---|---|---|---|---|---|---|---|
| SPLP Chol:DSPC:DODMA:PEG-DSG (55:20:15:10 mol ratio) | 0.078 | 0.16 | 108 | 36 | 0.6 | 0.65 | 3233 | 496 | |
| SPLP Chol:DSPC:DODMA:PEG-DSG (55:20:15:10 mol ratio) | 0.275 | 0.32 | 112 | 43 | 0.5 | 0.57 | 1430 | 878 | |
| Liposomes Chol:DSPC:DODMA:PEG-DSG (55:20:15:10 mol ratio) | 0.1 | 0.32 | 127 | 43 | 1.8 | 0.21 | 518 | 318 | |
| Liposomes Chol:DSPC:DODMA:PEG-DSG (55:20:15:10 mol ratio) | 0.4 | 0.32 | 112 | 14 | 0.3 | 0.83 | 2072 | 1272 | |
| Liposomes EPC:CHOL (55:45 mol ratio) | 0.275 | 0.32 | 125 | N/d | n/d | 0.57 | 1430 | 887 | |
| Liposomes EPC:CHOL (55:45 mol ratio) | 0.078 | 0.16 | 90 | 33 | 2.7 | 0.65 | 3233 | 503 | |
| PEI-SPLP Chol:DSPC:POPG:PEG-DSG (50:20:20:10 mol ratio) | 0.078 | 0.16 | 108 | N/d | N/d | 0.65 | 3233 | 503 | |

FIG. 14

N/d Not Determined.

LIPOSOMAL APPARATUS AND MANUFACTURING METHOD

CROSS-REFERENCES TO RELATED APPLICATIONS

This application is a divisional application of U.S. patent application Ser. No. 10/611,274, filed Jun. 30, 2003, which application claims priority to U.S. Provisional Application Ser. No. 60/392,887, filed Jun. 28, 2002, the disclosures of which are hereby incorporated by reference in their entirety.

BACKGROUND OF THE INVENTION

Many systems for administering active substances into cells are already known, such as liposomes, nanoparticles, polymer particles, immuno- and ligand-complexes and cyclodextrins (see, Drug Transport in antimicrobial and anticancer chemotherapy. G. Papadakou Ed., CRC Press, 1995). Liposomes are typically prepared in the laboratory by sonication, detergent dialysis, ethanol injection or dilution, French press extrusion, ether infusion, and reverse phase evaporation. Liposomes with multiple bilayers are known as multilamellar lipid vesicles (MLVs). MLVs are candidates for time release drugs because the fluids entrapped between layers are only released as each membrane degrades. Liposomes with a single bilayer are known as unilamellar lipid vesicles (UV). UVs may be made small (SUVs) or large (LUVs).

Some of the methods above for liposome production impose harsh or extreme conditions which can result in the denaturation of the phospholipid raw material and encapsulated drugs. In addition, these methods are not readily scalable for mass production of large volumes of liposomes. Further, lipid vesicle formation by conventional ethanol dilution, involves the injection or dropwise addition of lipid in an aqueous buffer. The resulting vesicles are typically heterogenous in size and contain a mixture of unilamellar and multilamellar vesicles.

Conventional liposomes are formulated to carry therapeutic agents either contained within the aqueous interior space (water-soluble drugs) or partitioned into the lipid bilayer(s) (water-insoluble drugs). Active agents which have short half-lives in the bloodstream are particularly suited to delivery via liposomes. Many anti-neoplastic agents, for example, are known to have a short half-life in the bloodstream such that their parenteral use is not feasible. However, the use of liposomes for site-specific delivery of active agents via the bloodstream is severely limited by the rapid clearance of liposomes from the blood by cells of the reticuloendothelial system (RES).

U.S. Pat. No. 5,478,860, which issued to Wheeler et al., on Dec. 26, 1995, and which is incorporated herein by reference, discloses microemulsion compositions for the delivery of hydrophobic compounds. Such compositions have a variety of uses. In one embodiment, the hydrophobic compounds are therapeutic agents including drugs. The patent also discloses methods for in vitro and in vivo delivery of hydrophobic compounds to cells.

PCT Publication WO01/05373 to Knopov, et al., which is incorporated by reference herein, discloses techniques for preparing lipid vesicles using an ethanol injection-type process with a static mixer that provides a turbulent environment (e.g., Reynolds numbers >2000). Therapeutic agents may then be loaded after vesicle formation Despite the apparent advances of U.S. Pat. No. 5,478,860 and WO05373, there exists a need for processes and apparatus for formulating and producing lipid vesicles, and in particular lipid vesicles encapsulating a therapeutic agent such as nucleic acid. The present invention fulfills these and other needs.

BRIEF SUMMARY OF THE INVENTION

The present invention provides processes and apparatus for making lipid vesicles that optionally contain a therapeutic agent. The therapeutic agent can include, for example, a protein, a nucleic acid, an antisense nucleic acid, a drug, or the like. The present invention can be used to form lipid vesicles that contain encapsulated plasmid DNA or small molecule drugs. In one aspect, the lipid vesicles are prepared rapidly at low pressure and the approach is fully scalable. In certain preferred embodiments, the process does not involve a static mixer or specialized extrusion equipment.

As such, in one embodiment, the present invention provides a process for producing a liposome. The process typically includes providing an aqueous solution in a first reservoir, the first reservoir in fluid communication with an organic lipid solution in a second reservoir, and mixing the aqueous solution with the organic lipid solution, wherein the organic lipid solution undergoes a continuous stepwise dilution to produce a liposome.

In certain aspects, the aqueous solution such as a buffer, comprises a therapeutic product, such that the therapeutic product is encapsulated in the liposome. Suitable therapeutic products include, but are not limited to, a protein, a nucleic acid, an antisense nucleic acid, a ribozyme, tRNA, snRNA, siRNA (small interfering RNA), pre-condensed DNA, and an antigen. In certain preferred aspects, the therapeutic product is nucleic acid.

In another embodiment, the present invention provides a process for producing a liposome encapsulating a therapeutic product. The process typically includes providing an aqueous solution in a first reservoir, and providing an organic lipid solution in a second reservoir, wherein one of the aqueous solution and the organic lipid solution includes a therapeutic product. The process also typically includes mixing the aqueous solution with the organic lipid solution, wherein the organic lipid solution mixes with the aqueous solution so as to substantially instantaneously produce a liposome encapsulating the therapeutic product. In certain aspects, the therapeutic product is a nucleic acid included in the aqueous solution. In certain aspects, the therapeutic product is lipophilic and is included in the organic lipid solution. In certain aspects, the initial therapeutic product encapsulation efficiency is as high as about 90%.

In still yet another embodiment, the present invention provides apparatus for producing a liposome encapsulating a therapeutic product. The apparatus typically includes a first reservoir for holding an aqueous solution, and a second reservoir for holding an organic lipid solution, wherein one of the aqueous solution and the organic lipid solution includes a therapeutic product. the apparatus also typically includes a pump mechanism configured to pump the aqueous and the organic lipid solutions into a mixing region at substantially equal flow rates. In operation, the organic lipid solution mixes with the aqueous solution in the mixing region to substantially instantaneously form a therapeutic product encapsulated liposome.

These and other aspects will be more apparent when read with the accompanying drawings and detailed descriptions that follow.

BRIEF DESCRIPTION OF THE DRAWINGS

FIG. 14 shows various parameters associated with flow in the T-connector of FIG. 13.

DETAILED DESCRIPTION OF THE INVENTION AND PREFERRED EMBODIMENTS

I. Definitions

Figure 1:
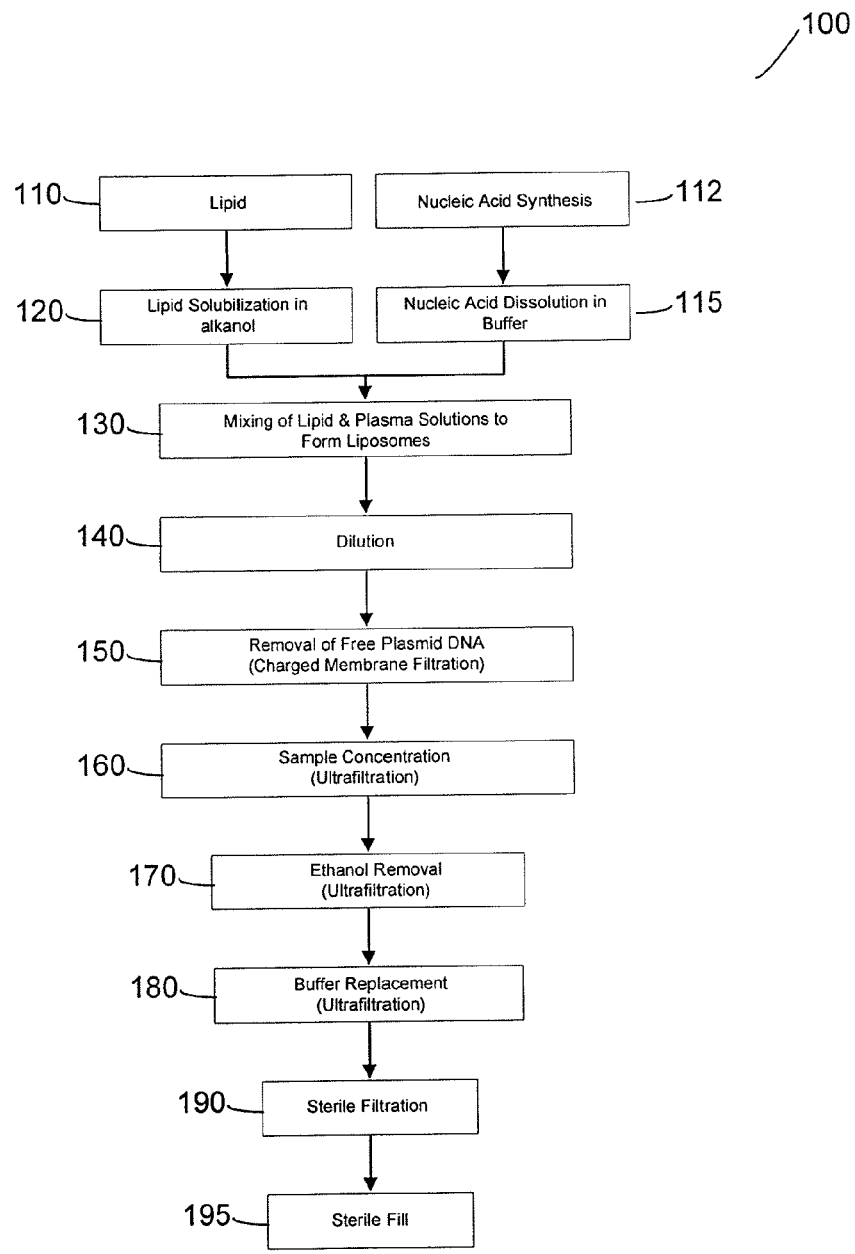
FIG. 1 provides a flow diagram for a manufacturing process according to one embodiment of the present invention.

The term "nucleic acid" refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), ribozymes, chimeric sequences, or derivatives of these groups.

"Antisense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, and other variants of the phosphate backbone of native nucleic acids. In addition, DNA and RNA may be single, double, triple, or quadruple stranded.

The term "gene" refers to a nucleic acid (e.g., DNA) sequence that comprises coding sequences necessary for the production of a polypeptide or precursor (e.g., herpes simplex virus). The polypeptide can be encoded by a full length coding sequence or by any portion of the coding sequence so long as the desired activity or functional properties (e.g., enzymatic activity, ligand binding, signal transduction, and the like) of the full-length or fragment are retained.

As used herein, the term "aqueous solution" refers to a composition comprising in whole, or in part, water.

As used herein, the term "organic lipid solution" refers to a composition comprising in whole, or in part, an organic solvent having a lipid.

The term "lipid" refers to a group of organic compounds that are esters of fatty acids and are characterized by being insoluble in water but soluble in many organic solvents. They are usually divided in at least three classes: (1) "simple lipids" which include fats and oils as well as waxes; (2) "compound lipids" which include phospholipids and glycolipids; (3) "derived lipids" such as steroids.

The term "amphipathic lipid" refers, in part, to any suitable material wherein the hydrophobic portion of the lipid material orients into a hydrophobic phase, while a hydrophilic portion orients toward the aqueous phase. Amphipathic lipids are usually the major component of a lipid vesicle. Hydrophilic characteristics derive from the presence of polar or charged groups such as carbohydrates, phosphato, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids. Additionally, the amphipathic lipid described above can be mixed with other lipids including triglycerides and sterols.

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, and other anionic modifying groups joined to neutral lipids.

The term "cationic lipid" refers to any of a number of lipid species which carry a net positive charge at a selective pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 3-(N-(N',N-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). The following lipids are cationic and have a positive charge at below physiological pH: DODAP, DODMA, DMDMA and the like.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid, with a reduced aqueous interior; or lipid aggregates or micelles, wherein the encapsulated component is contained within a relatively disordered lipid mixture.

As used herein, "lipid encapsulated" can refer to a lipid formulation which provides a compound with full encapsulation, partial encapsulation, or both.

As used herein, the term "SPLP" refers to a stable plasmid lipid particle. A SPLP represents a vesicle of lipids coating an interior comprising a nucleic acid such as a plasmid with a reduced aqueous interior.

II. General

The present invention provides processes and apparatus for making lipid vesicles. The processes can be used to make lipid vesicles possessing a wide range of lipid components including, but not limited to, cationic lipids, anionic lipids, neutral lipids, polyethylene glycol (PEG) lipids, hydrophilic polymer lipids, fusogenic lipids and sterols. Hydrophobic actives can be incorporated into the organic solvent (e.g., ethanol) with the lipid, and nucleic acid and hydrophilic actives can be added to an aqueous component. In certain aspects, the processes of the present invention can be used in preparing microemulsions where a lipid monolayer surrounds an oil-based core. In certain preferred aspects, the processes and apparatus are used in preparing lipid vesicles, or liposomes, wherein a therapeutic agent is encapsulated within a liposome coincident with liposome formation.

III. Processes of Making

FIG. 1 is an example of a representative flow chart 100 of a method of the present invention. This flow chart is merely an illustration and should not limit the scope of the claims herein. One of ordinary skill in the art will recognize other variations, modifications, and alternatives.

In one aspect, the present method provides a lipid solution 110 such as a clinical grade lipid synthesized under Good Manufacturing Practice (GMP), which is thereafter solubilized in an organic solution 120 (e.g., ethanol). Similarly, a therapeutic product, e.g., a therapeutic active agent such as nucleic acid 112 or other agent, is prepared under GMP. Thereafter, a therapeutic agent solution (e.g., plasmid DNA) 115 containing a buffer (e.g., citrate) is mixed with a lipid solution 120 solubilized in a lower alkanol to form a liposomal formulation 130. In preferred aspects of the present invention, the therapeutic agent is "passively entrapped" in the liposome substantially coincident with formation of the liposome. However, those of skill in the art will realize that the processes and apparatus of the present invention are equally applicable to active entrapment or loading of the liposomes after formation of the vesicle.

According to the processes and apparatus of the present invention, the action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in an hydration process with sufficient force to effectuate vesicle generation. By mixing the aqueous solution with the organic lipid solution, the organic lipid solution undergoes a continuous stepwise dilution in the presence of the buffer (aqueous) solution to produce a liposome.

In the processes of the present invention, the organic lipid solution preferably includes an organic solvent, such as a lower alkanol. In one aspect, the liposomes are then diluted 140 with a buffer (e.g., citrate) to increase nucleic acid (e.g., plasmid) entrapment. Before sample concentration 160, free therapeutic agent (e.g., nucleic acid) is removed by using, for example, an anion exchange cartridge 150. Further, by using an ultrafiltration step 170 to remove the alkanol, the sample is concentrated (e.g., to about 0.9 mg/mL plasmid DNA), the alkanol is removed, and the buffer is replaced with a substitute buffer (e.g., with a saline buffer) 180. Thereafter, the sample is filtered 190 and filled in vials 195. The process will now be discussed in more detail herein below using the steps as set forth in FIG. 1.

1. Lipid Solubilization and Therapeutic Agent Dissolution

In one embodiment, the liposome vesicles of the present processes are stable plasmid lipid particle (i.e., SPLP) formulations. Those of skill in the art will appreciate that the following description is for illustration purposes only. The processes of the present invention are applicable to a wide range of lipid vesicle types and sizes. These lipid vesicles include, but are not limited to, single bilayer lipid vesicles known as unilamellar lipid vesicles which can be made small (SUVs) or large (LUVs), as well as multilamellar lipid vesicles (MLVs). Further vesicles include, micelles, lipid-nucleic acid particles, virosomes, and the like. Those of skill in the art will know of other lipid vesicles for which the processes and apparatus of the present invention will be suitable.

The preferred size for liposomes made in accordance with the present processes and apparatus are between about 50-550 nm in diameter. In certain preferred aspects, the liposome preparation has a size distribution in which the mean size (e.g., diameter) is about 70 nm to about 300 nm, and more preferably the mean size is less than about 200 nm, such as about 150 nm or less (e.g., about 100 nm).

In certain aspects, the liposome formulation (e.g., SPLP formulation) of the present invention includes four lipid components: a phospholipid; cholesterol; a PEG-lipid; and a cationic lipid. In one preferred aspect, the phospholipid is DSPC, the PEG-lipid is PEG-DSG and the cationic lipid is DODMA. In one preferred aspect, the molar composition is about 20:45:10:25 DSPC:Chol:PEG-DSG:DODMA. In certain embodiments, the organic solvent concentration wherein the lipids are solubilized is about 45% v/v to about 90% v/v. In certain preferred aspects, the organic solvent is a lower alkanol. Suitable lower alkanols include, but are not limited to, methanol, ethanol, propanol, butanol, pentanol, their isomers and combinations thereof. In one embodiment, the solvent is preferably ethanol with a volume of about 50-90% v/v. Preferably, the lipids occupy a volume of about 1 mL/g to about 5 mL/g.

The lipids are solubilized 120 using for example, an overhead stirrer at a suitable temperature. In one aspect, the total lipid concentration of the solution is about 15.1 mg/mL (20 mM). In certain preferred aspects, the therapeutic agent (e.g., nucleic acid) is included in an aqueous solution (e.g., buffer) and is diluted to a final concentration. In one preferred aspect, for example, the final concentration is about 0.9 mg/mL in citrate buffer, with a pH of about 4.0. In this instance, the volume of the plasmid solution is the same as the alkanol-lipid solution. In one embodiment, the preparation of the therapeutic agent (e.g., nucleic acid) solution is performed in a jacketed stainless steel vessel with an overhead mixer. The sample does not need to be heated to be prepared, although in certain instances it is at the same temperature as the lipid solution prior to lipid vesicle formation.

In one embodiment, the therapeutic agent is included in the lipid solution. In certain preferred aspects, the therapeutic agent in the lipid solution is lipophilic. Suitable lipophilic agents include taxol, taxol derivatives, including, for example, protax III and paclitaxol, lipophilic benzoporphyrins, verteporfin the lipid prodrug of foscarnet, 1-O-octadecyl-sn-glycerol-3-phosphonoformate (ODG-PFA), dioleoyl [3H]iododeoxyuridine ([3H]IDU-Ol2), lipid derivatized HIV protease inhibitory peptides such as iBOC[L-Phe]-[D-beta-Nal]-Pip-[alpha-(OH)-Leu]-Val (7194) and other lipid derivatized drugs or prodrugs.

2. Liposome Formation

After the solutions, e.g., lipid solution 120 and aqueous therapeutic agent (e.g., nucleic acid) solution 115, have been prepared, they are mixed together 130 using, for example, a peristaltic pump mixer. In one aspect, the solutions are pumped at substantially equal flow rates into a mixing environment. In certain aspects, the mixing environment includes a "T"-connector or mixing chamber. In this instance, it is preferred that the fluid lines, and hence fluid flows, meet in a narrow aperture within the "T"-connector as opposing flows at approximately 180° relative to each other. Other relative introduction angles may be used, such as for example between 27° and 90° and between 90° and 180°. Upon meeting and mixing of the solution flows in the mixing environment, lipid vesicles are substantially instantaneously formed. Lipid vesicles are formed when an organic solution including dissolved lipid and an aqueous solution (e.g., buffer) are simultaneously and continuously mixed. Advantageously, and surprisingly, by mixing the aqueous solution with the organic lipid solution, the organic lipid solution undergoes a continuous stepwise dilution to substantially instantaneously produce a liposome. The pump mechanism can be configured to provide equivalent or different flow rates of the lipid and aqueous solutions into the mixing environment which creates lipid vesicles in a high alkanol environment.

Advantageously, and surprisingly, the processes and apparatus for mixing of the lipid solution and the aqueous solution as taught herein provides for encapsulation of therapeutic agent in the formed liposome substantially coincident with liposome formation with an encapsulation efficiency of up to about 90%. Further processing steps as discussed herein can be used to further refine the encapsulation efficiency and concentration if desired.

In one preferred aspect, using the processes and apparatus of the present invention, it is possible to form lipid vesicles instantaneously in a continuous two-step process that is fully scaleable. In one aspect, lipid vesicles are formed having a mean diameter of less than about 200 nm, which do not require further size reduction by high-energy processes such as membrane extrusion, sonication or microfluidization.

In one embodiment, lipid vesicles form when lipids dissolved in an organic solvent (e.g., ethanol) are diluted in a stepwise manner by mixing with an aqueous solution (e.g., buffer). This controlled stepwise dilution is achieved by mixing the aqueous and lipid streams together in an aperture, such as a T-connector. The resultant lipid, solvent and solute concentrations can be kept constant throughout the vesicle formation process.

Figure 2:
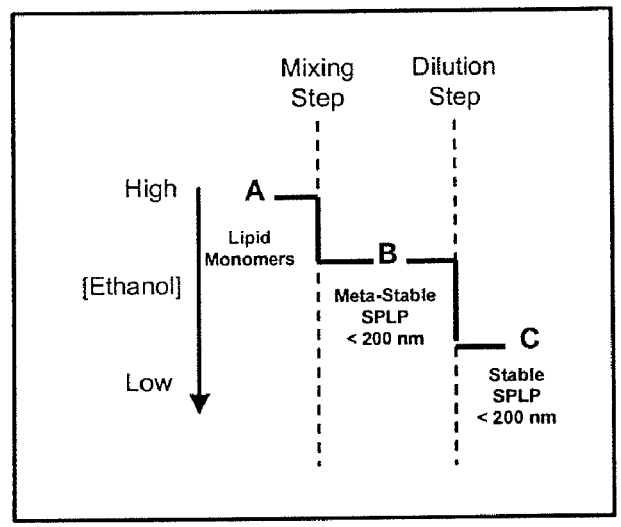
FIG. 2 provides a schematic of a process of making liposomes in one embodiment of the present invention.

One embodiment of the inventive process is shown in FIG. 2. In one aspect, using the processes of the present invention, a vesicle is prepared by a two-stage step-wise dilution without gradients. For example, in the first stepwise dilution, vesicles are formed in a high alkanol (e.g., ethanol) environment (e.g., about 30% to about 50% v/v ethanol). These vesicles can then be stabilized by lowering the alkanol (e.g., ethanol) concentration to less than or equal to about 25% v/v, such as about 17% v/v to about 25% v/v, in a stepwise manner. In preferred aspects, with therapeutic agent present in the aqueous solution, or in the lipid solution, the therapeutic agent is encapsulated coincident with liposome formation.

As shown in FIG. 2, in one embodiment, lipids are initially dissolved in an alkanol environment of about 40% v/v to about 90% v/v, more preferably about 65% v/v to about 90% v/v, and most preferably about 80% v/v to about 90% v/v (A). Next, the lipid solution is diluted stepwise by mixing with an aqueous solution resulting in the formation of vesicles at an alkanol (e.g., ethanol) concentration of between about 37.5-50% (B). By mixing the aqueous solution with the organic lipid solution, the organic lipid solution undergoes a continuous stepwise dilution to produce a liposome. Further, lipid vesicles such as SPLPs (a lipid-particle) can be further stabilized by an additional stepwise dilution of the vesicles to an alkanol concentration of less than or equal to about 25%, preferably between about 19-25% (C).

In certain aspects, for both stepwise dilutions (A→B and B→C), the resulting ethanol, lipid and solute concentrations are kept at constant levels in the receiving vessel. At these higher ethanol concentrations following the initial mixing step, the rearrangement of lipid monomers into bilayers proceeds in a more orderly fashion compared to vesicles that are formed by dilution at lower ethanol concentrations. Without being bound by any particular theory, it is believed that these higher ethanol concentrations promote the association of nucleic acid with cationic lipids in the bilayers. In one preferred aspect, nucleic acid encapsulation occurs within a range of alkanol (e.g., ethanol) concentrations above 22%.

In certain aspects, after the lipid vesicles are formed, they are collected in another vessel, for example, a stainless steel vessel. In one aspect, the lipid vesicles are formed at a rate of about 60 to about 80 mL/min. In one aspect, after the mixing step 130, the lipid concentration is about 1-10 mg/mL and the therapeutic agent (e.g., plasmid DNA) concentration is about 0.1-3 mg/mL. In certain preferred aspects, the lipid concentration is about 7.0 mg/mL and the therapeutic agent (e.g., plasmid DNA) concentration is about 0.4 mg/mL to give a DNA:lipid ratio of about 0.06 mg/mg. The buffer concentration is about 1-3 mM and the alkanol concentration is about 45% v/v to about 90% v/v. In preferred aspects, the buffer concentration is about 3 mM and the alkanol concentration is about 45% v/v to about 60% v/v.

3. Liposome Dilution

Turning back to FIG. 1, after the mixing step 130, the degree of therapeutic agent (e.g., nucleic acid) encapsulation can be enhanced if the lipid vesicle suspension is optionally diluted 140 prior to removal of free plasmid. For example, prior to dilution step 140, if the therapeutic agent entrapment is at about 30-40%, it can be increased to about 70-80% following incubation after the dilution step 140. In step 140, the liposome formulation is diluted to about 10% to about 40%, preferably about 20% alkanol, by mixing with an aqueous solution such as a buffer (e.g., 1:1 with citrate buffer, 100 mM NaCl, pH 4.0). Such further dilution is preferably accomplished with a buffer. In certain aspects, such further diluting the liposome solution is a continuous stepwise dilution. The diluted sample is then optionally allowed to incubate at room temperature.

4. Removal of Free Therapeutic agent

After the optional dilution step 140, about 70-80% or more of the therapeutic agent (e.g., nucleic acid) is entrapped within the lipid vesicle (e.g., SPLP) and the free therapeutic agent can be removed from the formulation 150. In certain aspects, anion exchange chromatography is used. Advantageously, the use of an anion exchange resin results in a high dynamic nucleic acid removal capacity, is capable of single use, may be pre-sterilized and validated, and is fully scaleable. In addition, the method preferably results in removal of free therapeutic agent (e.g., nucleic acid such as approximately 25% of total plasmid). The volume of sample after chromatography is unchanged, and the therapeutic agent (e.g., nucleic acid) and lipid concentrations are about 0.64 and 14.4 mg/mL, respectively. At this point, the sample can be assayed for encapsulated therapeutic agent and adjusted to about 0.55 mg/mL.

5. Sample Concentration

In certain instances, the liposome solution is optionally concentrated about 2-6 fold, preferably about 4 fold, using for example, ultrafiltration 160 (e.g., tangential flow dialysis). In one embodiment, the sample is transferred to a feed reservoir of an ultrafiltration system and the buffer is removed. The buffer can be removed using various processes, such as by ultrafiltration. In one aspect, buffer is removed using cartridges packed with polysulfone hollow fibers, for example, having internal diameters of about 0.5 mm and a 30,000 nominal molecular weight cut-off (NMWC). The liposomes are retained within the hollow fibers and recirculated while the solvent and small molecules are removed from the formulation by passing through the pores of the hollow fibers. In this procedure, the filtrate is known as the permeate solution. On completion of the concentration step, the therapeutic agent (e.g., nucleic acid) and lipid concentrations increase to about 0.90 and 15.14 mg/mL, respectively. In one embodiment, the alkanol concentration remains unchanged, but the alkanol:lipid ratio decreases about four fold.

6. Alkanol Removal

In one embodiment, the concentrated formulation is then diafiltrated against about 5-15 volumes, preferably about 10 volumes, of aqueous solution (e.g., buffer) (e.g., citrate buffer pH 4.0 (25 mM citrate, 100 mM NaCl) to remove the alkanol 170. The alkanol concentration at the completion of step 170 is less than about 1%. Preferably, lipid and therapeutic agent (e.g., nucleic acid) concentrations remain unchanged and the level of therapeutic agent entrapment also remains constant.

7. Buffer Replacement

After the alkanol has been removed, the aqueous solution (e.g., buffer) is then replaced by dialfiltration against another buffer 180 (e.g., against 10 volumes of saline 150 mM NaCl with 10 mM Hepes pH 7.4). Preferably, the ratio of concentrations of lipid to therapeutic agent (e.g., nucleic acid) remain unchanged and the level of nucleic acid entrapment is about constant. In certain instances, sample yield can be improved by rinsing the cartridge with buffer at about 10% volume of the concentrated sample. In certain aspects, this rinse is then added to the concentrated sample.

8. Sterile Filtration

In certain preferred embodiments, sterile filtration 190 of the sample at lipid concentrations of about 12-14 mg/mL can optionally be performed. In certain aspects, filtration is conducted at pressures below about 40 psi, using a capsule filter and a pressurized dispensing vessel with a heating jacket. Heating the sample slightly can improve the ease of filtration.

9. Sterile Fill

The sterile fill step 195 is performed using similar processes as for conventional liposomal formulations. The processes of the present invention result in about 50-60% of the input therapeutic agent (e.g., nucleic acid) in the final product. In certain preferred aspects, the therapeutic agent to lipid ratio of the final product is approximately 0.04 to 0.07.

IV. Therapeutic Agents

The lipid-based drug formulations and compositions of the present invention are useful for the systemic or local delivery of therapeutic agents or bioactive agents and are also useful in diagnostic assays. The following discussion refers generally to liposomes; however, it will be readily apparent to those of skill in the art that this same discussion is fully applicable to the other drug delivery systems of the present invention.

As described above, therapeutic agent is preferably incorporated into the lipid vesicle during formation of the vesicle. In one embodiment, hydrophobic actives can be incorporated into the organic solvent with the lipid, while nucleic acid and hydrophilic actives can be added to the aqueous component. In certain instances, the therapeutic agent includes one of a protein, a nucleic acid, an antisense nucleic acid, ribozymes, tRNA, snRNA, siRNA, pre-condensed DNA, an antigen and combinations thereof. In preferred aspects, the therapeutic agent is nucleic acid. The nucleic acid may encode a protein such as, for example, a herpes simplex virus, thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, or cytochrome P450 2B1.

In certain aspects, therapeutic agent is incorporated into the organic lipid component. In certain instances, the therapeutic agent is lipophilic. Suitable lipophilic agents include taxol, taxol derivatives, including, for example, protax III and Paclitaxol, lipophilic benzoporphyrins, verteporfin the lipid prodrug of foscarnet, 1-O-octadecyl-sn-glycerol-3-phosphonoformate (ODG-PFA), dioleoyl[3H]iododeoxyuridine ([3H] IDU-Ol2), lipid derivatized HIV protease inhibitory peptides such as iBOC-[L-Phe]-[D-beta-Nal]-Pip-[alpha-(OH)-Leu]-Val (7194) and other lipid derivatized drugs or prodrugs.

In another embodiment, the lipid vesicles of the present invention can be loaded with one or more therapeutic agents after formation of the vesicle. In certain aspects, the therapeutic agents which are administered using the present invention can be any of a variety of drugs which are selected to be an appropriate treatment for the disease to be treated. Often the drug is an antineoplastic agent, such as vincristine, doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues by the present processes. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-conversants, e.g., phenyloin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

V. Apparatus

Figure 3:
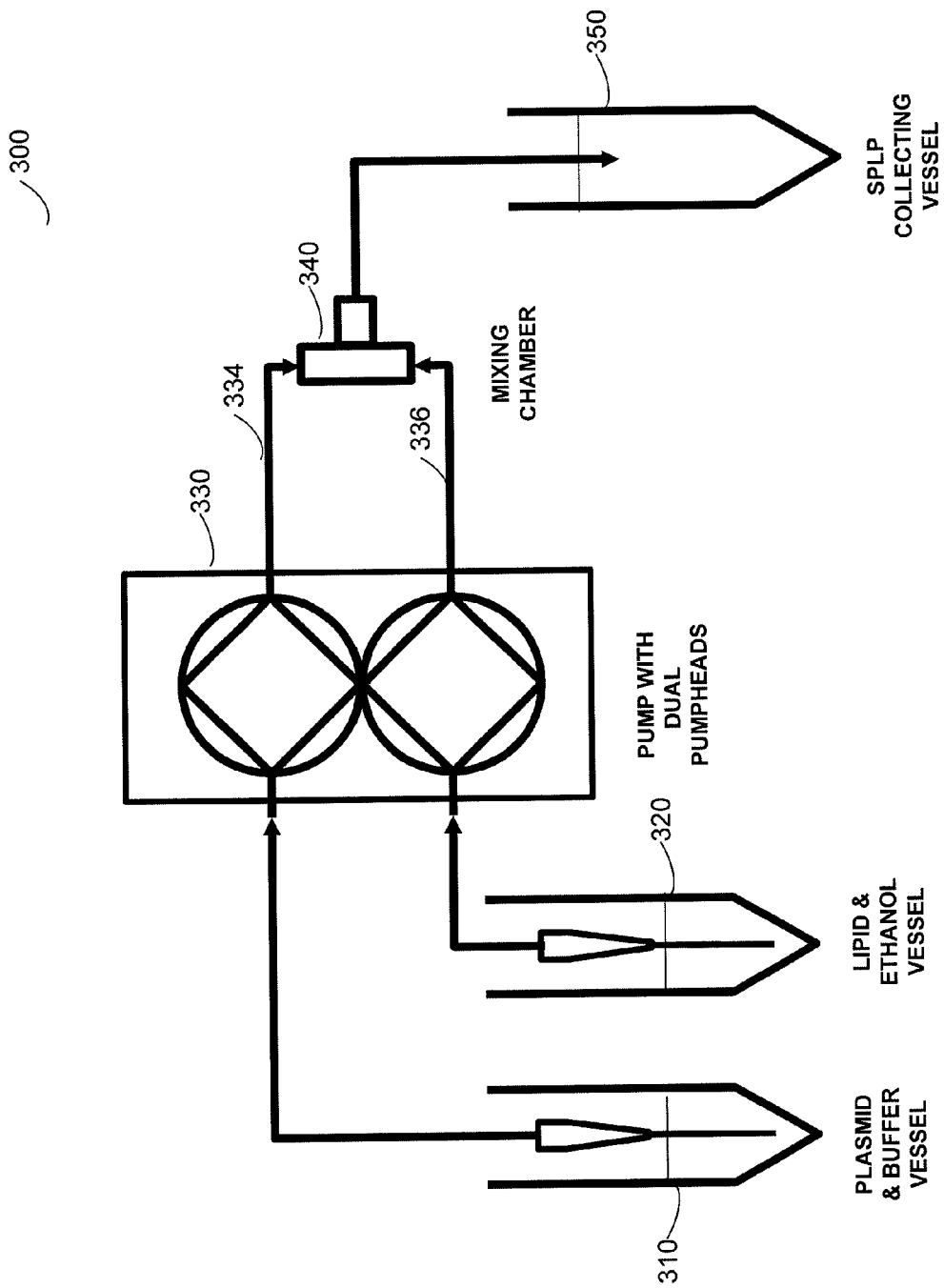
FIG. 3 provides a schematic of an apparatus according to one embodiment of the present invention.

In another embodiment, the present invention provides apparatus for carrying out the processes of the present invention. FIG. 3 is an example of a representative schematic of an apparatus 300 according to one embodiment of the present invention. This schematic is merely an illustration and should not limit the scope of the claims herein. One of ordinary skill in the art will recognize other variations, modifications, and alternatives.

In one embodiment, the apparatus of the present invention includes two reservoirs, an aqueous solution reservoir 310 and an organic solution reservoir 320, for holding aqueous solution and organic solution, respectively. In certain aspects, the lipid vesicle formulations are prepared rapidly, at low pressure (e.g., <10 psi) and the apparatus and processes of the present invention are fully scaleable (e.g., 0.5 mL-5000 L). At a 1-L scale, lipid vesicles are formed at about 0.4-0.8 L/min. In certain preferred aspects, the apparatus do not use static mixers nor specialized extrusion equipment.

The mixing chamber 340 is, in one embodiment, a T-connector, having optional hose barbs, wherein fluid lines 334 and 336 impact each other at about 180°. The angle of mixing can also be changed, and lipid vesicles less than about 100 nm can be formed at angles of between about 27° and about 90° or even between 90° and 180°. In preferred aspects, lipid vesicles of well defined and reproducible mean diameters are prepared using substantially equal flow rates of the flow lines. In other aspects, lipid vesicles of well defined and reproducible mean diameters are prepared by changing the flow rate of the fluid lines, e.g., to ensure sufficient mixing in some cases. In preferred aspects, the variance between flow rates is less that 50%, more preferably less than about 25% and even more preferably less than about 5%.

Figure 13:
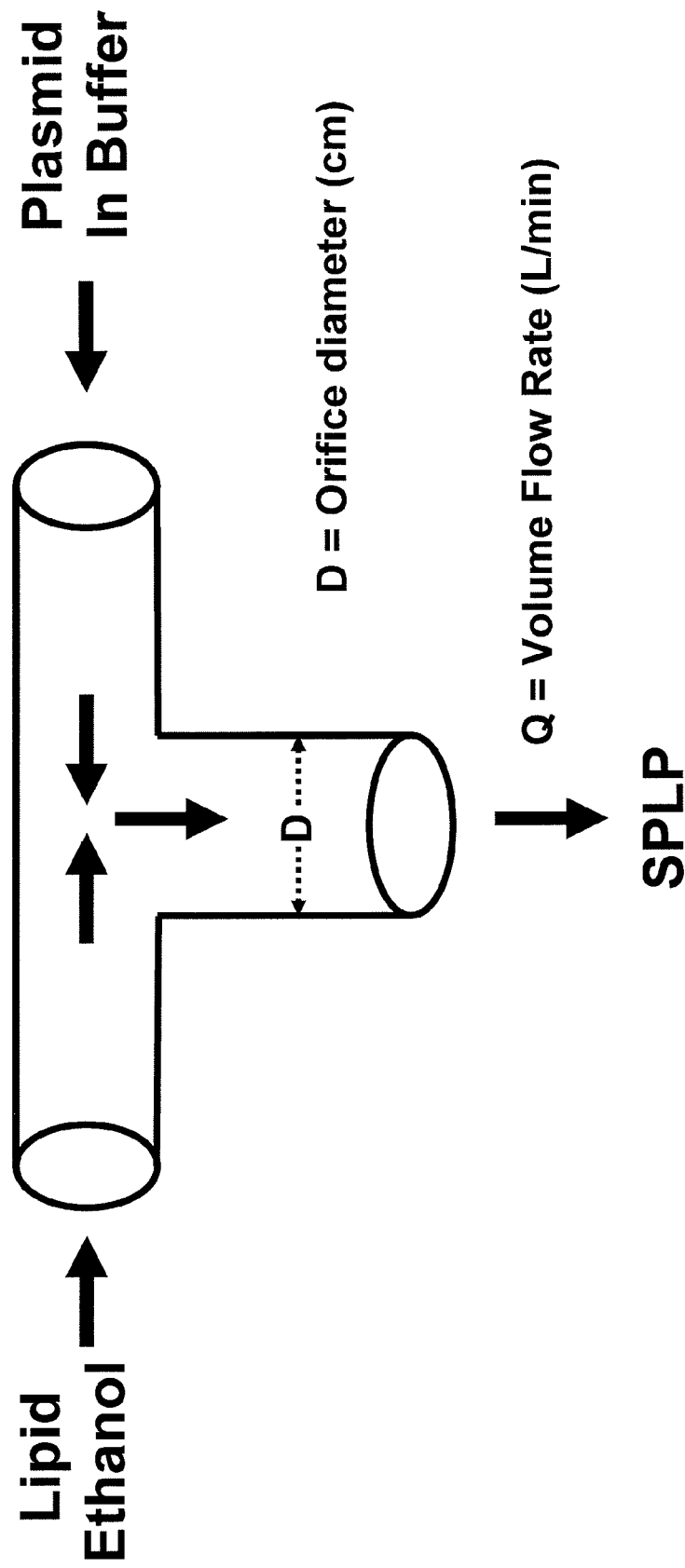
FIG. 13 shows a T-connector and associated flow dynamics according to one embodiment.

FIG. 13 shows a T-connector and associated flow dynamics according to one embodiment. Examples of flow rates, and resulting shear rates and Reynolds numbers (turbulence measure) are shown in FIG. 14 and discussed in more detail hereafter in Example 8. In comparison with prior systems, the present invention provides non-turbulent flow and increased shear rates at much lower (and substantially equivalent) flow rates. For example, the present invention advantageously provides non-turbulent flow ($N_{re}$<2000) in the mixing environment with a shear rate between about 500/s and about 3300/s at a flow rate (both flow lines) of between about 0.075 and about 0.3 L/min.

Mixing of the two fluid components can be driven using, for example, a peristaltic pump 330, a positive displacement pump, or by pressurizing both the lipid-ethanol and buffer vessels 320, 310. In one aspect, a Watson-Marlow 505 Di/L pump fitted with a 505 L pump head is used; silicone tubing (e.g., platinum cured with 3.2 mm ID, 2.4 mm wall thickness; available from Watson Marlow as catalog no. 913A032024) can be used for flow lines into a polypropylene or stainless steel T-connector (e.g., with a ⅛" ID). Lipid vesicles are typically formed at room temperature, but lipid vesicles may be formed at elevated temperatures according to the present invention. Unlike other existing approaches, there are no general requirements for buffer composition. In fact, the processes and apparatus of the present invention can formulate a lipid vesicle by mixing lipid in an alkanol with water. In certain aspects, the processes and apparatus of the present invention form lipid vesicles that are less than 200 nm in diameter.

When lipid vesicles are prepared containing plasmid DNA (such as SPLPs), the ratio of plasmid to cationic lipid and counter ions can be optimized. For refined formulations, 70-95% plasmid DNA ("pDNA") encapsulation after mixing, and ethanol removal steps is preferred. The level of pDNA encapsulation can be increased by diluting this initial SPLP formulation. Surprisingly, the processes and apparatus of the present invention provide an encapsulation efficiency, upon mixing the solutions (with therapeutic agent in one of the solution components) in the mixing environment, of up to about 90%. Further refinement, e.g., dilution, may be performed as discussed herein.

In certain aspects, liposome producing apparatus 300 of the present invention further includes a temperature control mechanism (not shown) for controlling the temperature of the reservoirs 310 and 320. Preferably, fluid from the first reservoir 310 and the second reservoirs 320 flows into mixing chamber 340 simultaneously at separate apertures. Apparatus 300 further includes a collection reservoir 350 downstream of the mixing chamber for liposome collection. Moreover, in certain aspects, apparatus 300 further includes storage vessels upstream of either or both of the reservoirs 310 and 320. Further, either or both of the reservoirs 310 and 320 are preferably jacketed stainless steel vessels equipped with an overhead mixer.

Figure 4:
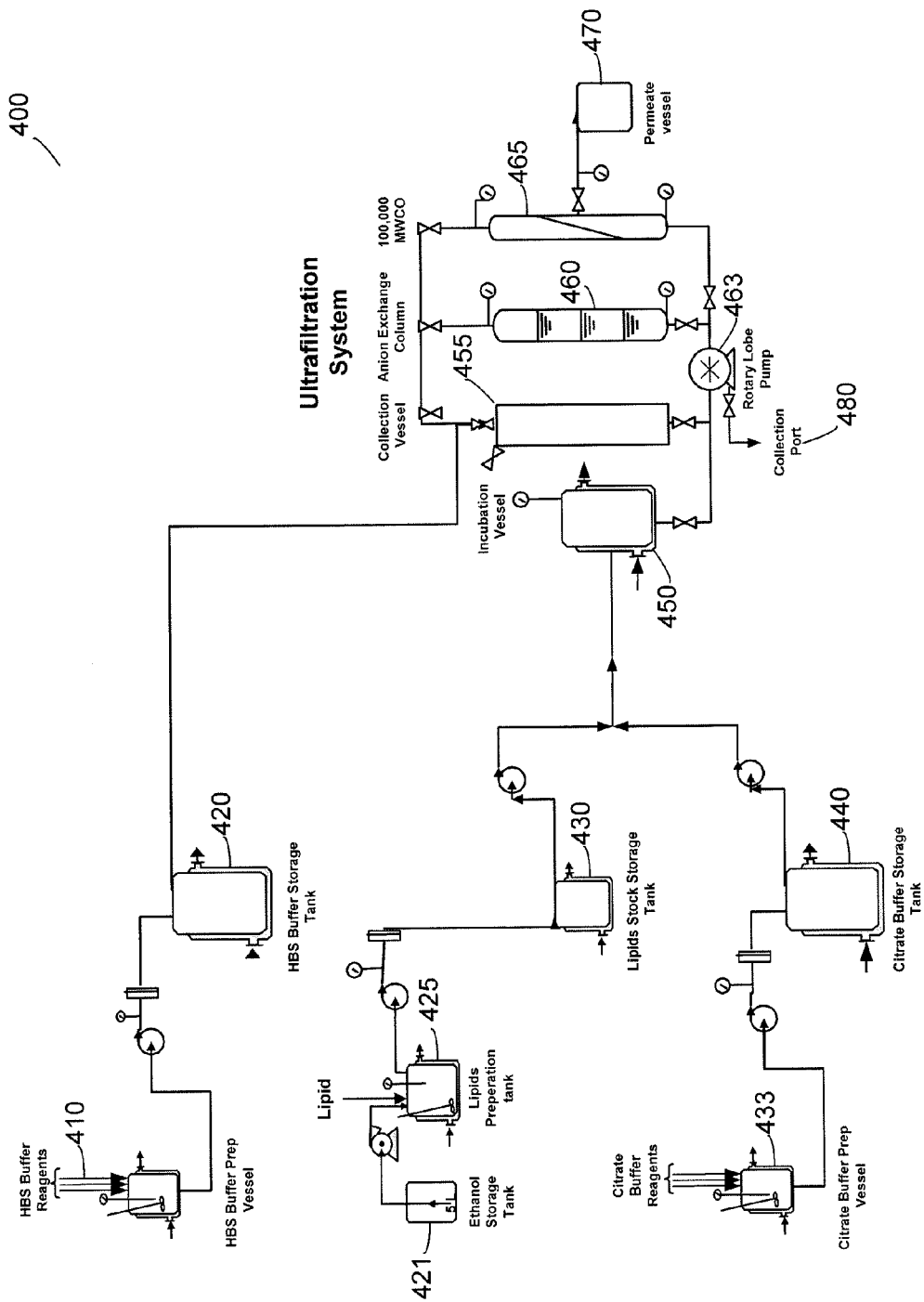
FIG. 4 provides a schematic of an apparatus having an ultrafiltration system according to one embodiment of the present invention.

In another embodiment, the present invention provides an apparatus having an ultrafiltration system for carrying out the processes of the present invention. FIG. 4 is an example of a representative schematic of an apparatus 400 according to one embodiment of the present invention. This schematic is merely an illustration and should not limit the scope of the claims herein. One of ordinary skill in the art will recognize other variations, modifications, and alternatives.

In certain aspects, apparatus 400 includes a plurality of reservoirs and is equipped with an ultrafiltration system. An aqueous solution reservoir 440 and an organic solution reservoir 430 each have upstream preparation vesicles 433 and 425, respectively. In one aspect, lipid preparation vessel 425 is optionally equipped with an alkanol storage vessel 421 in fluid communication therewith.

As shown in FIG. 4, the ultrafiltration system includes an incubation vessel 450 in fluid communication with a collection vessel 455, an exchange column 460 and a tangential flow ultrafiltration cartridge 465. The ultrafiltration system optionally includes a permeate vessel 470. In certain aspects, ultrafiltration is used to concentrate SPLP samples and then remove ethanol from the formulation by buffer replacement.

In one embodiment of operation, the diluted SPLPs are transferred to the feed reservoir of the ultrafiltration system. Concentration is performed by removing buffer and ethanol using, for example, cross flow cartridges 465 packed with polysulfone hollow fibers that possess internal diameters of about 0.5 mm and a 100,000 molecular weight cut-off (MWCO). The SPLPs are retained within the hollow fibers and re-circulated, whereas the ethanol and buffer components are removed from the formulation by passing through the pores of these hollow fibers. This filtrate is known as the permeate solution and is discarded via vessel 470. After the SPLPs are concentrated to the desired plasmid concentration, the buffer in which the SPLPs are suspended is removed by ultrafiltration and replaced by an equal volume of the final buffer. Ultrafiltration can be replaced with other methods such as conventional dialysis.

VI. Examples

Example 1

This Example illustrates various physical and chemical properties of SPLPs made in accordance with one embodiment of the present invention.

Table I the amount of ethanol, pDNA and lipid content in process steps according to the present invention.

TABLE I

| STEP | % Initial Volume | [Ethanol] (%) | [pDNA] (mg/ml) | pDNA Recovery (%) | [Lipid] (mg/ml) | Lipid Recovery (%) |
|---|---|---|---|---|---|---|
| SPLP formation | 100 | 45 | 0.45 | 95 | 7.6 | 95 |
| Dilution | 200 | 22.5 | 0.23 | 90 | 3.8 | 90 |
| Concentration | 50 | 22.5 | 0.90 | 90 | 15.1 | 90 |
| Ethanol removal | 50 | <1% | 0.90 | 90 | 15.1 | 90 |
| Buffer replacement* | 45 | <0.1% | 0.90 | 81 | 15.1 | 81 |
| Free DNA Removal** | 45 | <0.1% | 0.64 (0.55) | 55 | 14.4 (12.4) | 76 |
| Sterile filtration & Vial fill*** | 49 | <0.1% | 0.50 | 50 | 11.1 | 68 |

*Estimate 10% total volume and SPLP loss after buffer replacement step.
**Assume that 75% of pDNA is encapsulated and all free DNA is removed. Estimate 5% loss of SPLP on anion exchange cartridge. At this step the sample will be assayed for encapsulated pDNA and adjusted to 0.55 mg/ml to anticipate loss of SPLP during the filtration step (concentrations after adjustment to 0.55 mg/ml pDNA shown in brackets).
***Assume a maximum 5% volume loss and up to 10% total SPLP loss.

Table II sets forth the plasmid specification made according to one aspect of the present invention.

TABLE II

Plasmid Specification

| | Test | Specification |
|---|---|---|
| 1. | Appearance | Clear, Colorless solution. |
| 2. | Electrophoresis | Relative migration vs standard. |
| 3. | Circular plasmid | >90% |
| 4. | Potentiometric pH value | 6.5-8.5 |
| 5. | Electrophoresis | RNA undetectable |
| 6. | BCA protein assay | Undetectable |
| 7. | Spectrometric $A_{260}/A_{280}$ | 1.7-2.0 |
| 8. | DNA hybridization assay | <1% E. coli DNA |
| 9. | Sterility Testing | No growth observed in bacteriologic media |
| 10. | LAL | <20 EU/mg. |
| 11. | UV Absorbance | 2.0-3.0 mg/mL. |

Table III sets forth the SPLP specification made according to one aspect of the present invention.

TABLE III

| | Test | Specification |
|---|---|---|
| 1. | Appearance | Homogenous, opaque white solution |
| 2. | pH | 7.4 (6.0-8.5) |
| 3. | Osmolality | 320 mOsm/kg (290-500 mOsm/kg) |
| 4. | Plasmid Content | 0.5 mg/mL (0.25-1.0 mg/mL) |
| 5. | DSPC Content | 20 +/− 4.0 mol % |
| 6. | DODMA Content | 25 +/− 5.0 mol % |
| 7. | PEG-DSG Content | 10 +/− 2.0 mol % |
| 8. | Cholesterol Content | 45 +/− 5.0 mol % |
| 9. | Particle size | Mean diameter 100 ± 25 nm |
| 10. | Plasmid Encapsulation | >85% |
| 11. | Plasmid Integrity | >80% |
| | Supercoiled | |
| | Nicked | <20% |
| | Linear | <2% |
| 12. | LAL | <50 EU/mg DNA |
| 13. | Sterility | Pass |

Example 2

This Example illustrates various process parameters in one embodiment of the present invention.

Figure 5:
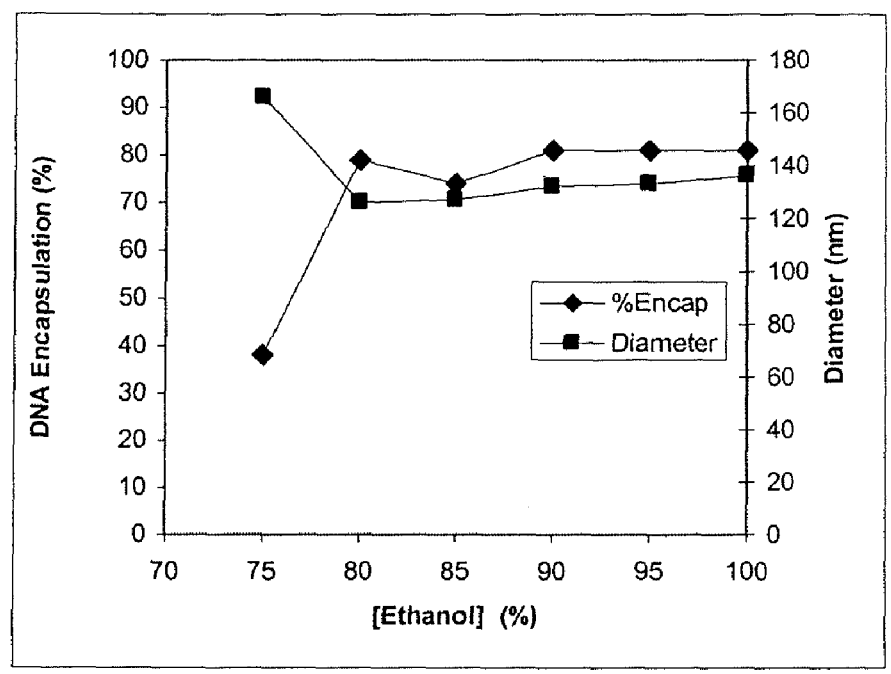
FIG. 5 shows the effect of varying the ethanol concentration of the initial lipid solution on SPLP mean diameter and DNA encapsulation. DNA encapsulation efficiency and vesicle sizes determined after the dilution step.

In one SPLP embodiment, varying the initial ethanol concentration for lipid dissolution had little impact on either vesicle size or DNA encapsulation, providing that the ethanol concentration was high enough to ensure that none of the individual lipid components precipitated (see, FIG. 5). Below 75% ethanol, lipids were not soluble even with heating to 55° C. Lipids dissolved in 75% ethanol at 55° C. formed SPLP with larger mean diameters and lower DNA encapsulation (see, FIG. 5).

The initial DNA to lipid ratio has been varied from 0.048-0.081 mg DNA: mg lipid formulation and vesicles of similar size with 77-90% DNA encapsulation were formed.

Figure 6:
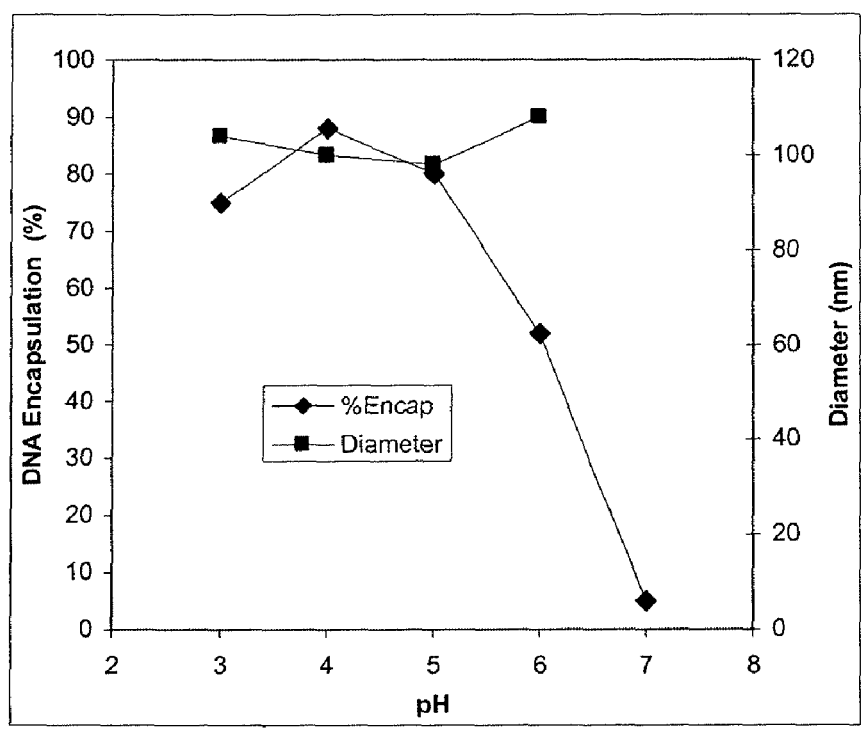
FIG. 6 shows the effect of varying pH of the initial plasmid solution on SPLP mean diameter and DNA encapsulation. DNA encapsulation efficiency and vesicle sizes were determined after the dilution step.

SPLPs have been prepared at a pH range of about 3.5-6 for the initial mixing step and all formulations possessed mean particle diameters of less than 150 nm and DNA encapsulation efficiencies of greater than 50% (see, FIG. 6). At higher pH, vesicles can also be prepared with similar vesicle sizes, but with lower DNA encapsulation efficiencies.

In certain aspects, mean vesicle diameters of empty vesicles prepared using one process of the present invention depend upon the salt concentration of the diluting buffer, (e.g., Sphingomyelin:cholestesterol vesicles, EPC:EPG vesicles). Varying the ionic conditions in the buffer, influences the tendency for a given lipid to arrange itself into bilayers and vesicles.

Figure 7:
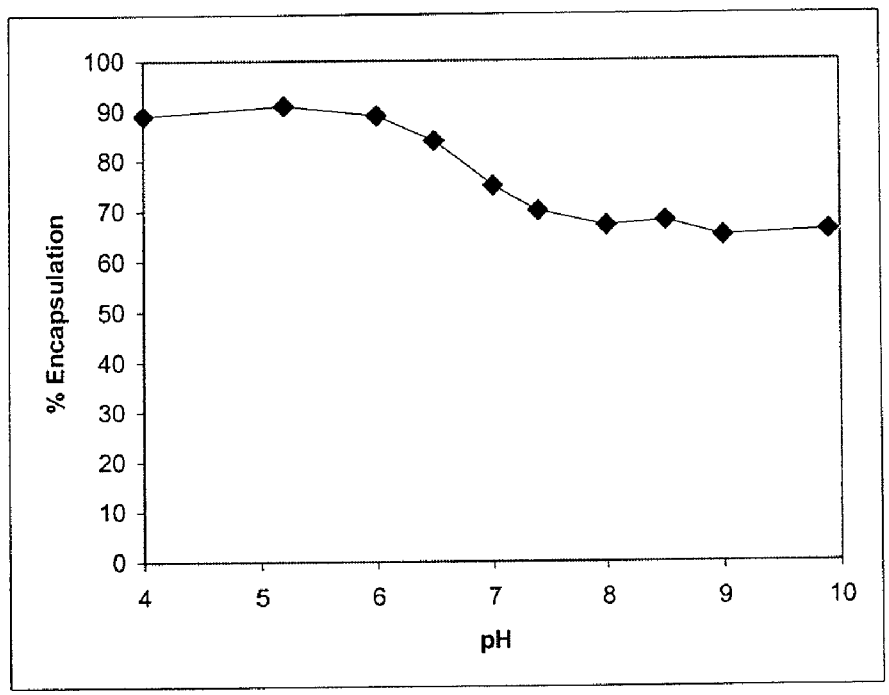
FIG. 7 shows the effect of varying pH of the buffer used for the dilution step on pDNA encapsulation efficiency.
Figure 8:
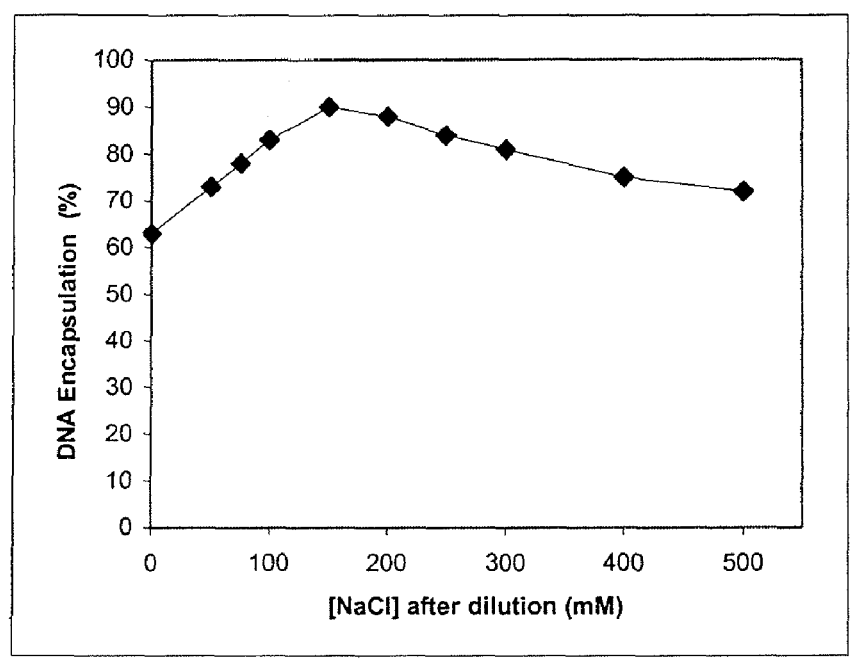
FIG. 8 shows the effect of varying the salt concentration of the buffer used for the dilution step on pDNA encapsulation efficiency.

During the development of one SPLP formulation, it was found that both the pH and salt concentration of the diluting buffer had a significant effect on the DNA encapsulation efficiency. Naturally, diluting buffers with pH values lower than the pKa for the cationic lipid component (DODMA) gave higher encapsulation values (FIG. 7). Interestingly, a final salt concentration of 150 mM was also optimal for DNA encapsulation (FIG. 8).

Example 3

This Example illustrates the use of one process of the present invention to make EPC and POPC vesicles.

POPC vesicles are useful as "sink" vesicles for membrane fusion assays. In particular, they can be used in excess to remove PEG lipids from other liposomes, thus destabilizing the other liposomes and allowing them to fuse with the desired membrane. EPC vesicles are useful for removing cholesterol from arterial plaques.

The vesicles were prepared at an initial ethanol concentration of 80%, and lipid concentration of 10 mM. After mixing and dilution, the ethanol concentration was 20%, and lipid concentration was 5 mM. The EPC formulation was mixed and diluted with PBS, and the POPC was mixed and diluted with HBS. Both preparations were concentrated and ethanol removed using an ultrafiltration cartridge, i.e., the EPC against PBS, and the POPC against HBS. Both preparations were then sterile filtered using 0.22 um syringe filters.

TABLE IV

EPC and POPC vesicle data

| Sample | Lot Number | Vesicle Size (nm) | | | Lipid Concentration mg/mL |
|---|---|---|---|---|---|
| | | Diam | SD | Chi$^2$ | |
| POPC | 25031302-02 | 125 | 62 | 7 | 22.0 |
| EPC | 25031302-01 | 89 | 39 | 9 | 18.2 |

Example 4

This Example illustrates the use of one process of the present invention to make EPC/Cholesterol vesicles with a pH gradient.

Unilamellar lipid vesicles (LUV) comprising EPC and Cholesterol have traditionally been prepared by hydrating lipid films to form multilamellar lipid vesicles (MLV) that have been subjected to vesicle size reduction using high-pressure extrusion. It is well known that these vesicles can be prepared with acidic aqueous interiors and a pH gradient across the lipid bilayer. Weakly basic lipophilic molecules have been shown to accumulate in these vesicles at high internal concentrations. Various drug-loaded liposomes that are currently in late stage clinical trials utilize this approach (e.g., Myocet: doxorubicin loaded vesicles).

Figure 9A:
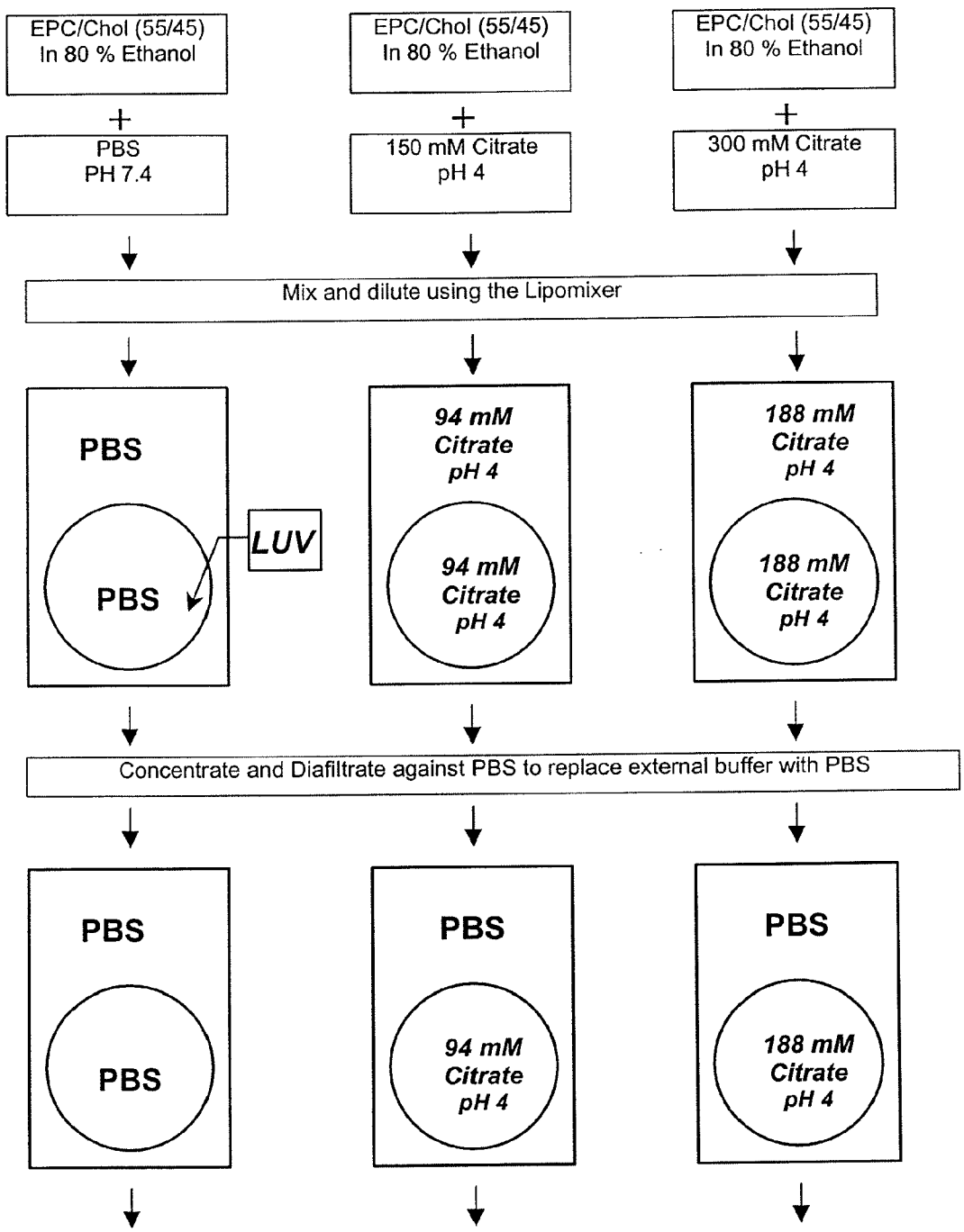
FIG. 9A-B shows a schematic process of making liposomes of the present invention.
Figure 9B:
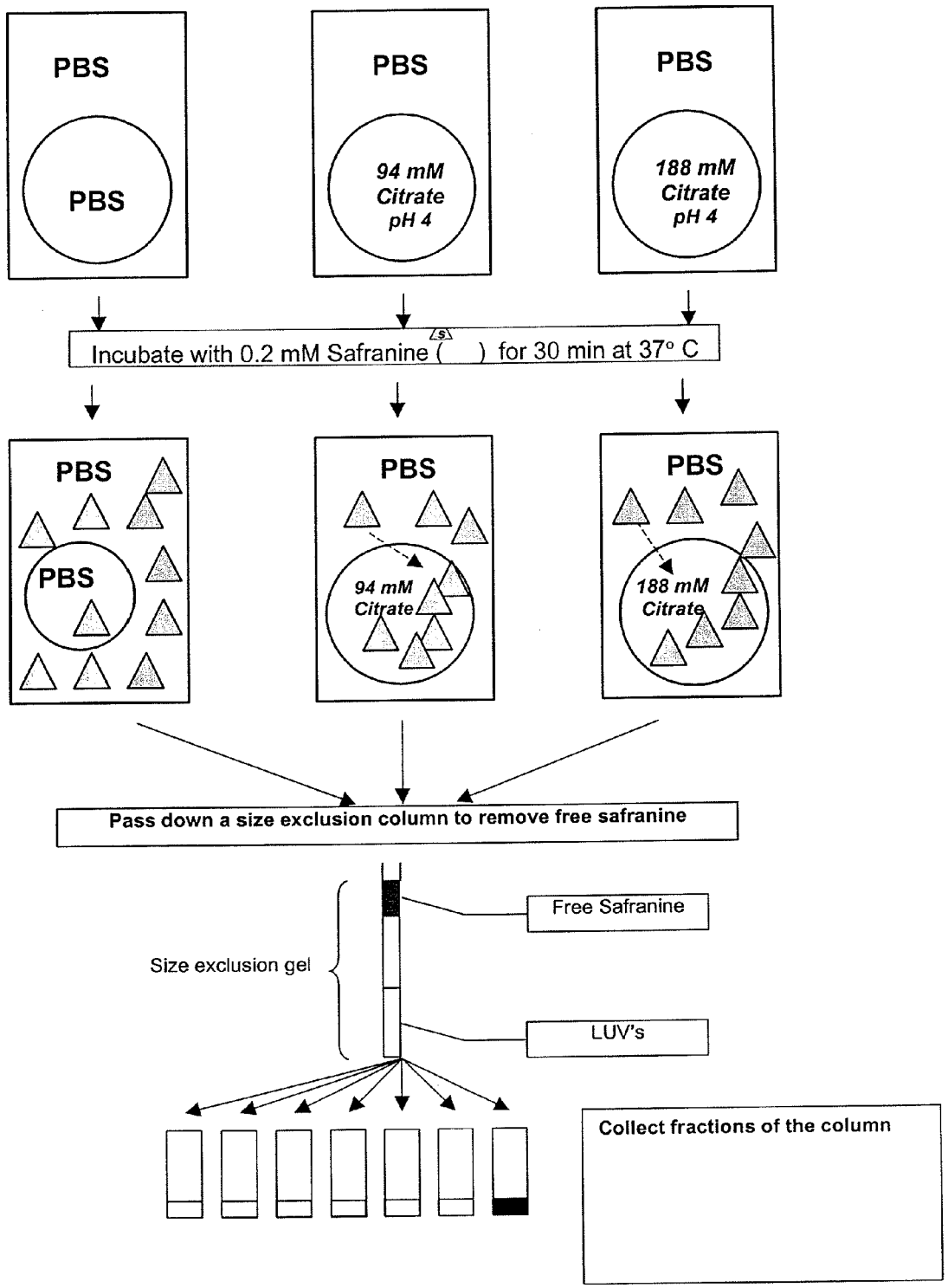

In one aspect, safranine was used to determine whether such a pH gradient was present. Safranine is a lipophilic basic dye that has been used to study membrane pH gradients EPC/Chol vesicles were prepared using the present processes and apparatus at an initial ethanol concentration of 80%, and lipid concentration of 10 mM (See FIG. 9A-B). After mixing and dilution, the ethanol concentration was 20%, and lipid concentration was 5 mM. Three different formulations were prepared:

1. Mixed and diluted with PBS (control).
2. Mixed and diluted with 150 mM citrate (final citrate concentration is 94 mM).
3. Mixed and diluted with 300 mM citrate (final citrate concentration is 188 mM).

After mixing and dilution, each sample was concentrated and ethanol was removed using ultrafiltration. After the concentration step, each sample was diafiltrated against its diluting buffer to ensure that the acidic citrate buffer present within vesicles would not leak out during ethanol removal. All samples were finally formulated with an external buffer of phosphate-buffered saline at pH 7.4. After sterile filtration, the mean vesicle diameters of these formulations were very similar (90-92 nm) and possessed acceptable standard deviation and Chi squared values (Table V).

Following dialysis, the vesicles were assayed for lipid concentration using the Infinity cholesterol assay. Solutions were then prepared containing 5 mM lipid and 0.2 mM safranine obtained from a filtered 10 mM stock solution. The solutions were incubated at 37° C. for 30 minutes. A 500 ul aliquot of each incubated solution was then passed down a 2-mL Sepharose CL4B gel filtration column. The free dye was separated from the vesicles, and the lipid-containing fractions were collected and analyzed. The safranine concentration was determined by measuring the fluorescence of the samples at 516 nm excitation and 585 nm emission.

Figure 10:
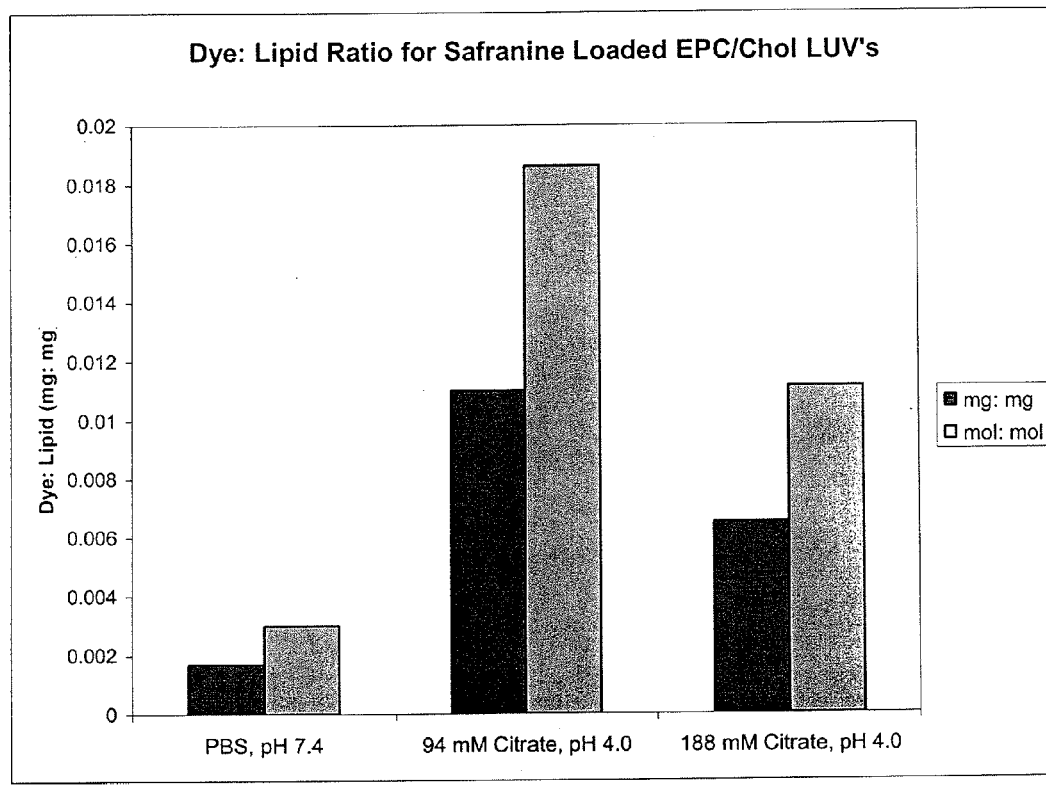
FIG. 10 shows encapsulation of safranine in certain liposomes of the present invention.

The vesicles with acidic interiors accumulated safranine, with the 94 mM citrate-containing vesicles showing the highest encapsulation. In contrast, the PBS control vesicles encapsulated very little safranine. The 188 mM citrate vesicles also encapsulated some safranine, but not as much as the 94 mM citrate-containing vesicles (See FIG. 10).

TABLE V

Safranine- Loaded EPC/Chol Vesicles

| Sample | Safranine Encapsulation | Vesicle Size (nm) | | | Dye:Lipid Ratio | |
|---|---|---|---|---|---|---|
| | | Diam | SD | Chi$^2$ | Mg:mg | mol:mol |
| PBS Control | 9% | 90 | 33 | 2.7 | 0.002 | 0.003 |
| 94 mM Citrate | 54% | 92 | 41 | 1.7 | 0.011 | 0.019 |
| 188 mM Citrate | 31% | 91 | 35 | 4.8 | 0.007 | 0.011 |

Example 5

This Example illustrates the use of one process of the present invention to make sphingomyelin/cholesterol vesicles.

Sphingomyelin/cholesterol vesicles are desirable due to their durability and strength. These vesicles can also be used to encapsulate drugs using a pH gradient. However, these LUV have traditionally needed to be formed at temperatures greater than 65° C. and using high pressure extrusion. In order to form these vesicles with the lipomixer, a number of variables needed to be taken into consideration, such as ethanol concentration, lipid concentration, and the salt concentration of the mixing and dilution buffer.

The vesicles were formulated at a ratio of 55/45 SM/Chol (mol:mol), while the initial ethanol concentration after mixing varied from 50 to 25%. Dilution buffers tested included PBS, water, 10 mM citrate, 150 mM citrate, and 300 mM citrate. Final lipid concentrations ranged from 0.5 to 2.5 mM.

The vesicles formulated in the presence of salt (i.e., using buffers) were 200-500 nm, indicating an MLV. Aliquots of these samples were dialyzed against both 150 mM citrate and water in an attempt to remove ethanol and stabilize the vesicles.

Example 6

This Example illustrates the use of one process of the present invention to prepare vesicles that passively encapsulation small molecules such as calcein.

Figure 11:
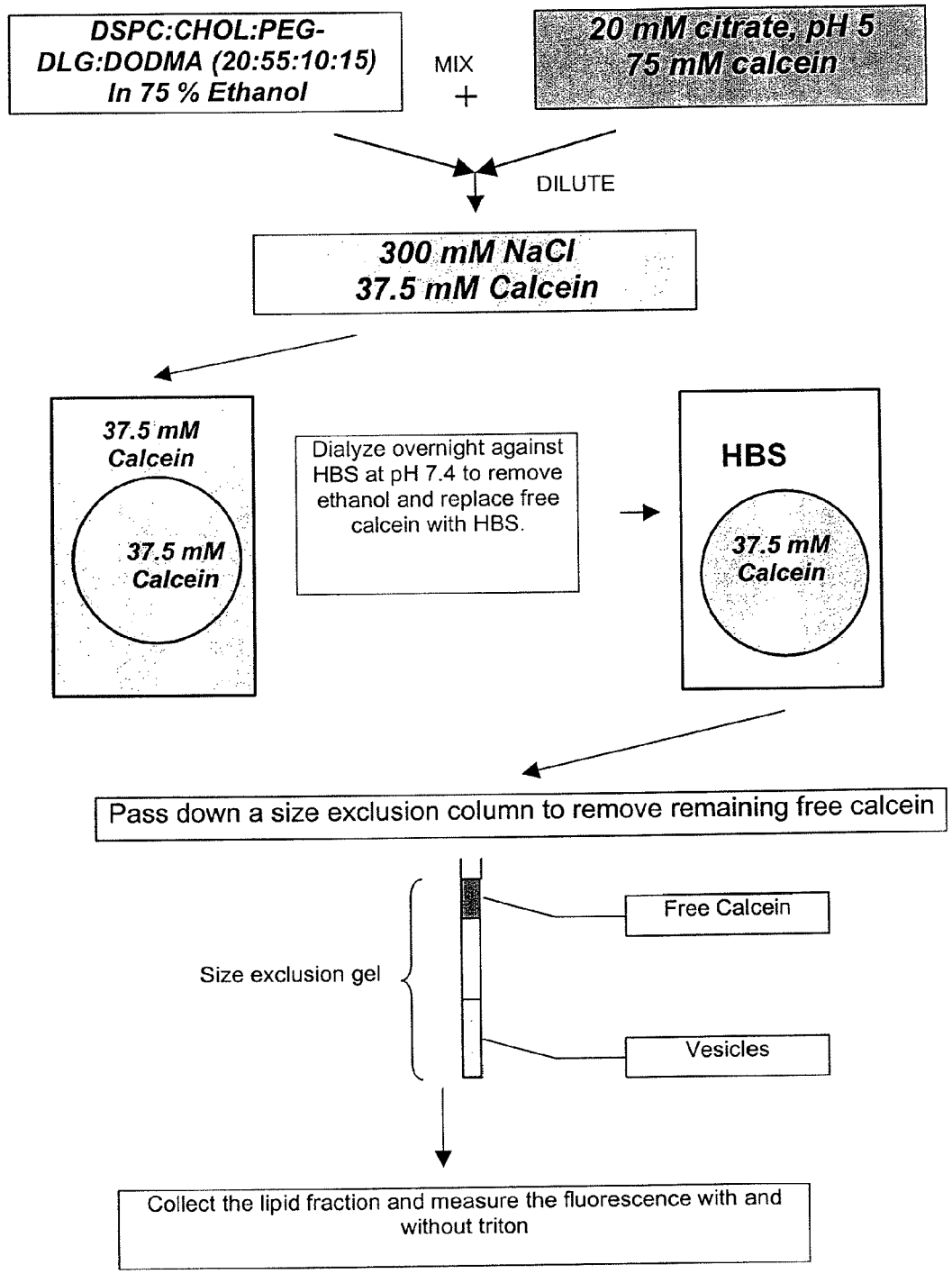
FIG. 11 shows a schematic process of making liposomes of the present invention.

Calcein is a fluorescent dye that is self-quenching at concentrations greater than 10 mM. Vesicles encapsulating calcein can be used in fusion assays to determine whether vesicles have fused together. Fusion decreases the internal calcein concentration, causing it to fluoresce. Vesicles were prepared with DSPC:CHOL:PEG-DLG:DODMA (20:55:10:15) at an ethanol concentration of 19% and 2 mM lipid after mixing and dilution (See FIG. 11). Lipids dissolved in ethanol were mixed with a solution containing 20 mM citrate and 75 mM calcein, and then the resulting vesicles were diluted with 300 mM NaCl and 37.5 mM Calcein. The calcein was obtained from a 100 mM stock solution. The final calcein concentration in the vesicles was 37.5 mM.

After mixing and dilution the vesicles were dialyzed overnight against HBS to remove unencapsulated dye. This was unsuccessful at removing all of the free dye, so the vesicles were passed down a gel filtration column. The lipid fraction was collected and analyzed. It was found that the calcein was indeed self quenching at the concentration inside the vesicles. This is a clear demonstration that the processes and apparatus of the present invention can be used to prepare vesicles that passively encapsulate small molecules.

TABLE VI

| | Calcein-encapsulated vesicles | | | | |
|---|---|---|---|---|---|
| | Vesicle Size (nm) | | | Fluorescence | |
| Step | Diam | SD | Chi$^2$ | rF$_{without\ triton}$ | rF$_{with\ triton}$ |
| Post Dilution | 205 | 109 | 0.4 | N/d | N/d |
| Post Dialysis | 173 | 74 | 0.5 | N/d | N/d |
| Post Gel Filtration | 178 | 77 | 5.4 | 0.4 | 4.1 |

Example 7

This Example illustrates the use of one process of the present invention versus prior art methods.

Figure 12:
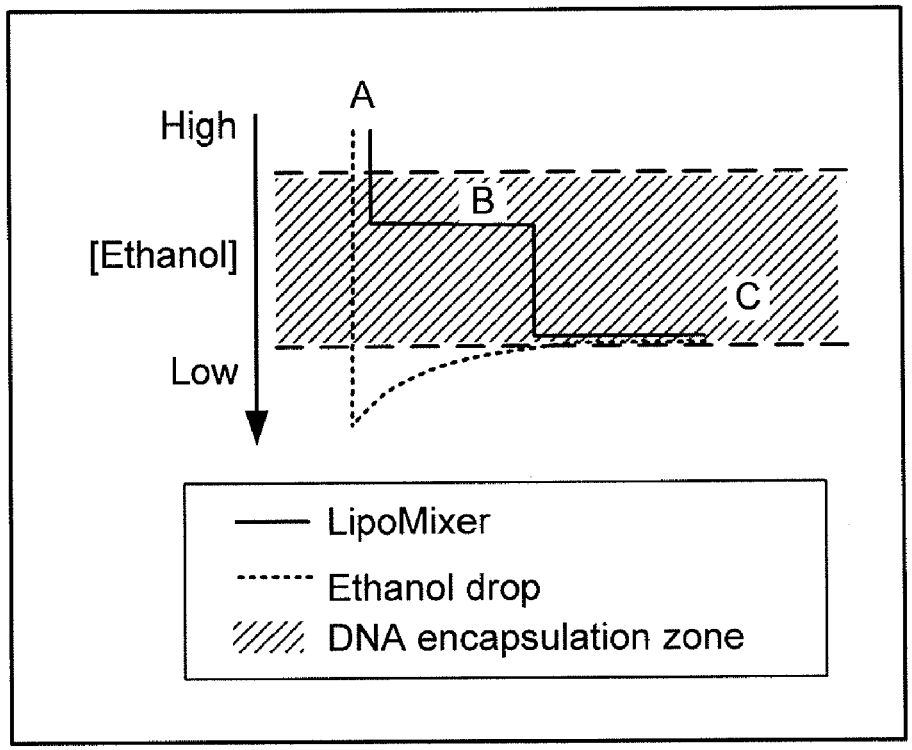
FIG. 12 illustrates a comparison between one embodiment of the present invention and an ethanol drop method for encapsulating pDNA.

With reference to FIG. 12, lipids were dissolved in 90% ethanol (A) and diluted either: step-wise using an apparatus of the present invention to 45% (B) and 22.5% ethanol (C), represented by the solid line ("LipoMixer"); or added drop-wise with into stirred buffer to a final ethanol concentration of 22.5% (C), represented by the dotted line. Even though the final ethanol concentrations for both preparations were the same, the SPLP formed according to the processes of the present invention had 85% DNA encapsulation whereas vesicles prepared by ethanol drop had only 5% DNA encapsulation.

Example 8

This example illustrates various conditions and properties for forming liposomes according to the present invention. It should be appreciated that other conditions and parameters may be used and that those used herein are merely exemplary.

With reference to FIGS. 13 and 14, various flow rates (substantially equivalent for both lipid and aqueous solution flows) are modeled and analyzed to show various parameters such as shear rate and Reynolds number ($N_{re}$) and vesicle size. Parameters and conditions were determined at the outlet of the T-connector correcting for the density and viscosity of the resulting ethanol solution. Additional turbulence as a result of the two streams meeting one another in opposition has not been accounted for, nor has additional turbulence as a result of the streams having to turn a 90 degree corner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus for producing a lipid vesicle encapsulating a nucleic acid within the lipid vesicle, said apparatus comprising:
   a first reservoir for holding an aqueous solution including a nucleic acid;
   a second reservoir for holding an organic lipid solution, wherein the lipids present in said organic lipid solution are solubilized in a lower alkanol at a concentration of about 75% v/v to 100% v/v; and
   a pump mechanism configured to pump said aqueous solution and said organic lipid solution into a mixing environment at about equal flow rates;
   wherein said organic lipid solution mixes with said aqueous solution in the mixing environment to instantaneously produce a lipid vesicle encapsulating the nucleic acid within the lipid vesicle by diluting said lower alkanol to a concentration of between 45% v/v to about 60% v/v; and
   wherein the mixing environment includes a T-connector, wherein said aqueous solution and said organic lipid solution are introduced into the T-connector as opposing flows at about 180° relative to each other and mixed within the T-connector.

2. The apparatus of claim 1, wherein said nucleic acid is selected from the group consisting of a plasmid, an antisense polynucleotide, a ribozyme, tRNA, snRNA, siRNA, and pre-condensed DNA.

3. The apparatus of claim 1, wherein said nucleic acid comprises an siRNA.

4. The apparatus of claim 1, wherein said lower alkanol is selected from the group consisting of methanol, ethanol, propanol, butanol, pentanol, isomers thereof, and combinations thereof.

5. The apparatus of claim 1, wherein said lower alkanol comprises ethanol.

6. The apparatus of claim 1, wherein the lipid vesicle is a liposome.

7. The apparatus of claim 1, wherein one or both of the first and the second reservoirs are temperature controlled.

8. The apparatus of claim 1, wherein one or both of the first and the second reservoirs include a jacketed stainless steel vessel with an overhead mixer.

9. The apparatus of claim 1, wherein the T-connector is polypropylene or stainless steel.

10. The apparatus of claim 1, wherein the lipids present in said organic lipid solution comprise a phospholipid, cholesterol, a PEG-lipid, and a cationic lipid.

11. The apparatus of claim 1, wherein the apparatus further comprises a tangential flow ultrafiltration system.

12. The apparatus of claim 1, wherein the lipids present in said organic lipid solution are solubilized in said lower alkanol at a concentration of 100% v/v.

13. The apparatus of claim 1, wherein the pump mechanism comprises a peristaltic pump.

* * * * *